US006303820B1

(12) United States Patent
Giera et al.

(10) Patent No.: US 6,303,820 B1
(45) Date of Patent: Oct. 16, 2001

(54) PROCESS FOR THE PREPARATION OF NITROSOBENZENES

(75) Inventors: Henry Giera, Grosskitzighofen; Walter Lange, Odenthal; Michaela Meiers, Speyer; Raul Pires, Leverkusen, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/707,188

(22) Filed: Nov. 6, 2000

(30) Foreign Application Priority Data

Nov. 12, 1999 (DE) ............................... 199 54 396

(51) Int. Cl.$^7$ ..................... C07C 205/06; C07C 211/46
(52) U.S. Cl. ..................... 564/305; 568/939; 568/940
(58) Field of Search ................... 568/939, 940; 564/305

(56) References Cited

FOREIGN PATENT DOCUMENTS

| 1680689 | 9/1991 | (RU) . |
|---|---|---|
| 2042661 | 8/1995 | (RU) . |
| 2044724 | 9/1995 | (RU) . |
| 2090542 | 9/1997 | (RU) . |

OTHER PUBLICATIONS

Database Caplus on STN, Acc. No. 1995:954279, Hanson et al., 'Catalysts for the oxidative bromination of aromatic amines and their N–acetyl derivatives.' J. Chem. Res., Synop. (1995), (11), p. 457 (abstract), 1995.*
Database WPI, Section Ch, Week 199401, Derwent Publications Ltd., London, GB; Class B05, AN 1994–005122, XP002161864 & SU 1 781 207 A (Sibe Techn Inst), Dec. 15, 1992.

Porta, F. et al, "Catalytic Synthesis of C–Nitroso Compounds by Cis–Mo(0)2(acac)2" J. Mol. Catal, A:Chem. (2000), 157 (1–2), 123–129, XP000982547.
Journal of Organic Chemistry, vol. 60, No. 5, Mar. 10, 1995, pp. 1326–1331, Zuolin Zhu et al, "Kinetics and Mechanism of Oxidation of Anilines by Hydrogen Peroxide as Catalyzed by Methylrhenium Trioxide".
Vogle'Textbook of Quantitative Chem. Analysis, 5th ed. Longivan Scientific & Tech., (date unavailable) pp. 235–254, "Gas Chromatography".
Analytische Chemie fur die Praxis, (month unavailable) 1982, pp. 37–41, "Kontroll–Methoden für Ergebnisse" .
Journal of Organic Chemistry, vol. 58, No. 14, Jul. 2, 1993, pp. 3633–3638, Sigeki Sakaue et al, "Oxidation of Aromatic Amines with Hydrogen Peroxide Catalyzed by Cetylpyridinium Heteropolyoxometalates".
J. Chem. Soc., Chem. Commun. (month unavailable) 1993, pp. 1510–1511, Stefan Tollari et al, "Catalytic Oxidation of Primary Aromatic Amines to the Corresponding Nitroso Compounds by $H_2O_2$ and $[Mo(O)(O_2)_2(H_2O)(hmpa)]$ (hmpa = Hexamethylphosphoric Triamide)".
Journal Organic Chemistry, vol. 31, No. 12, (month unavailable) 1995, pp. 1640–1642, E. B. Mel'nikov et al, "Oxidation of Primary Aromatic Amines, Catalyzed by Tungsten Compounds*".

\* cited by examiner

Primary Examiner—Johann Richter
Assistant Examiner—Brian J. Davis
(74) Attorney, Agent, or Firm—Joseph C. Gil; Noland J. Cheung

(57) ABSTRACT

The invention relates to a process for the preparation of nitrosobenzenes from aromatic amines by oxidation with hydrogen peroxide in the presence of sodium molybdate dihydrate and an inert organic solvent.

3 Claims, No Drawings

PROCESS FOR THE PREPARATION OF NITROSOBENZENES

FIELD OF THE INVENTION

The invention relates to a process for the preparation of nitrosobenzenes from aromatic amines by oxidation with hidrogen peroxide in the presence of a catalyst and a suitable inert organic solvent.

BACKGROUND OF THE INVENTION

The preparation of nitrobenzene, which is an important intermediate, is known and can be carried out by various methods. It can be used for the synthesis of antioxidants and stabilizers in the rubber and polymers industry, and in particular for the production of 4-aminodiphenylamine (4-ADPA).

One method for the preparation of nitrosobenzenes is oxidation of corresponding aromatic amines with suitable oxidation agents, such as hydrogen peroxide, in the presence of a catalystic and in the presence of a suitable solvent.

The preparation of nitrosobenzenes from aromatic by catalytic oxidation with hydrogen peroxide is described, for example by S. Sakaue, T. Tsubakino, Y. Nishiyama, Y. Ishii. *Org. Chem.* 1993, 58, 3633; S. Tollari, M. Cuscela, F. Porta, *J. Chem. Soc., Chem. Commun.* 1993, 1510; and in RU-A 2042661; RU-A 2044724; RU-A 20905642; and by E. B. Mel'nikov, G. A. Suboch. E. Yu. Belyaev. *Russ. J. Org. Chem.* 1995, 31, 160–1642; and Z. Zhu, J.H. Espensen, *J. Org. Chem.* 1995, 60, 1326–1332

Disadvantages of the process mentioned are, for example, the use of high-risk solvents, such as chloroform, in amounts which are not practicable on a large industrial scale in order to achieve good yields, the use of toxic compounds, such as hexamethylphosphoric acid triamide, in the preparation of the catalyst, the use of additional co-catalysts and the use of relatively large amounts of catalyst, as well as the use of expensive catalysts. Because of the disadvantages mentioned, a process operated on a large industrial scale would be uneconomical, associated with extensive safety measures.

It has now been found that nitrosobenzenes can be prepared from aromatic amines by catalytic oxidation with hydrogen peroxides in an industrially simple manner and avoiding the disadvantages described above if the oxidation is carried out in the presence of sodium molybdate as the catalyst.

SUMMARY OF THE INVENTION

The present invention therefore provides a process for the preparation of nitrosobenzenes of the general formula

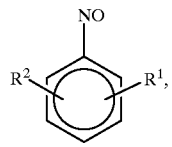

wherein
  $R^1$ and $R^2$ are identical or different and represent hydrogen, $C_1$-$C_4$-alkyl or $C_1$-$C_4$-alkoxy,
  by oxidation of corresponding aromatic amines in the presence of an inert organic solvent or solvent mixture, which is characterized in that the oxidation is carried out with hydrogen peroxide in the presence of sodium molybdate dihydrate at temperatures of 5 to 25° C. at a molar ratio of aromatic amines to hydrogen peroxide to sodium molybdate dihydrate of (1):(2.0 to 5.0):(0.001 to 0.05). Preferably aromatic amines, such as for example aniline, o-, ni- and p-toluidine and o-, m-, and p-anisidine, are use and particularly preferably aniline.

DETAILED DESCRIPTION OF THE INVENTION

Nitrosobenzenes of the above formula in which $R^1$ and $R^2$ represent hydrogen or methyl or methoxy groups are preferably prepared. The preparation of nitrosobenzene (i.e., $R^1$ and $R^2$=hydrogen) is especially preferred.

The process according to the invention is preferably carried out at temperatures of 15 to 25° C.

The hydrogen peroxide employed according to the present invention is conventionally employed in the aqueous form in a concentration of 15 to 80, preferably 30 to 50 wt. % hydrogen peroxide.

Possible inert organic solvents are, in particular, those which are practically immiscible with water and are capable of forming a second (organic) phase in the reaction mixture.

Organic solvents: cyclohexane, petroleum ether, toluene and/or methylene chloride, in particular cyclohexane, petroleum ether and/or toluene are most preferred.

As mentioned, the inert organic solvents, which are practically immiscible with water, can be employed in mixtures with one another. The most favorable mixing ratio can easily be determined by appropriate preliminary experiments, as can the amount of inert organic solvents.

The process according to the present invention is preferably carried out at a molar ratio of aromatic amines to hydrogen peroxide to sodium molybdate dihydrate of (1):(2.5 to 4.5):(0.005 to 0.02).

Once nitrosobenzene have been prepared according to the present invention, the resulting nitrosobenzene can be isolated from the reaction mixture in a conventional manner, for example, by separating off the organic phase, washing with an NaCl solution and removing the solvent employed.

The nitrosobenzenes are obtained in yields of 64 to 92% of theory and in purities of ≧95%.

The invention is further illustrated but is not intended to be limited by the following examples in which all parts and percentages are by weight unless otherwise specified.

EXAMPLES

General working instructions:

The catalyst is initially introduced into the reaction vessel, 1 mmol (93.13 mg) aniline dissolved in 2.5 ml solvent are added and hydrogen peroxide is added. After 4 hours, the reaction is terminated and the yield is determined by a GC method in accordance with 1.) Vogel's, Textbook of Quantitative Chemical Analysis, 5th Edition, Longwan Scientific & Technical, p. 247

2.) H. Hulpke, H. Hartkamp, G. Tölg (ed.), Analytische Chemie für die Praxis, K. Beyermnann, Organische Spurenanalyse, G. Thieme Verlag, Stuttgart, N. Y., 1982, p. 37–41.

TABLE

Summary of the examples

| Example no. | Solvent | Amount of cat. (eq) | Amount of H$_2$O$_2$ (eq) | Yield (%) |
|---|---|---|---|---|
| 1 | cyclohexane | 0.02 | 3.0 | 87 |
| 2 | cyclohexane | 0.02 | 3.4 | 90 |
| 3 | cyclohexane | 0.01 | 3.0 | 84 |
| 4 | cyclohexane | 0.01 | 3.4 | 88 |
| 5 | petroleum ether | 0.02 | 3.0 | 90 |
| 6 | petroleum ether | 0.02 | 3.4 | 92 |
| 7 | petroleum ether | 0.01 | 3.0 | 89 |
| 8 | petroleum ether | 0.01 | 3.4 | 88 |
| 9 | toluene | 0.02 | 3.0 | 67 |
| 10 | toluene | 0.02 | 3.4 | 69 |
| 11 | toluene | 0.01 | 3.0 | 64 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of nitrosobenzenes of the general formula

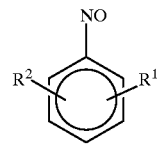

wherein
R$^1$ and R$^2$ are identical or different and represent hydrogen, C$_1$-C$_4$-alkyl or C$_1$-C$_4$-alkoxy,
comprising the step of oxidizing of corresponding aromatic amines in the presence of an inert organic solvent or solvent mixture, wherein the oxidation is carried out with hydrogen peroxide in the presence of sodium molybdate dihydrate at temperatures of 5 to 25° C. at a molar ratio of aromatic amines to hydrogen peroxide to sodium molybdate dihydrate of (1):(2.0 to 5.0):(0.001 to 0.05).

2. A process for the preparation of nitrosobenzenes according to claim 1, wherein said molar ratio of aromatic amines to hydrogen peroxide to sodium molybdate dihydrate is (1):(2.5 to 4.5):(0.005 to 0.02).

3. A process for the preparation of nitrosobenzenes according to claim 1, wherein said inert organic solvent is selected from the group consisting of cyclohexane, petroleum ether, toluene, methylene chloride and mixtures thereof.

* * * * *